(12) United States Patent
Finkel (10) Patent No.: US 11,931,171 B2
(45) Date of Patent: Mar. 19, 2024

(54) BIOASSAY FOR THE NON-INVASIVE DETECTION OF DRUG USE AND PHYSIOLOGIC CONDITIONS

(71) Applicant: CHILDREN'S NATIONAL MEDICAL CENTER, Washington, DC (US)

(72) Inventor: Julia C. Finkel, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 813 days.

(21) Appl. No.: 16/963,123

(22) PCT Filed: Jan. 15, 2019

(86) PCT No.: PCT/US2019/013671
§ 371 (c)(1),
(2) Date: Jul. 17, 2020

(87) PCT Pub. No.: WO2019/143620
PCT Pub. Date: Jul. 25, 2019

(65) Prior Publication Data
US 2021/0045679 A1 Feb. 18, 2021

Related U.S. Application Data

(60) Provisional application No. 62/619,434, filed on Jan. 19, 2018.

(51) Int. Cl.
*A61B 5/00* (2006.01)
*A61B 3/11* (2006.01)
(Continued)

(52) U.S. Cl.
CPC ............ *A61B 5/4845* (2013.01); *A61B 3/112* (2013.01); *A61B 3/145* (2013.01); *A61B 5/163* (2017.08); *G16H 50/20* (2018.01); *G16H 50/70* (2018.01)

(58) Field of Classification Search
CPC ....... A61B 5/4845; A61B 3/112; A61B 3/145; A61B 5/163; A61B 5/1128; A61B 3/0025;
(Continued)

(56) References Cited

U.S. PATENT DOCUMENTS 9,357,966 B1 6/2016 Cohen
2002/0024633 A1 2/2002 Kim et al.
(Continued)

FOREIGN PATENT DOCUMENTS

CN 104586386 A 5/2015
CN 104586410 A 5/2015
(Continued)

OTHER PUBLICATIONS

Office Action dated Dec. 6, 2022 in Japanese Patent Application No 2020-539732 (with English translation), 14 pages.
(Continued)

*Primary Examiner* — Mohammed A Hasan
(74) *Attorney, Agent, or Firm* — Oblon, McClelland, Maier & Neustadt, L.L.P.

(57) ABSTRACT

The present disclosure is related to a method and apparatus for determining drug usage or a physiological characteristic of a patient. The present disclosure describes acquiring a video sequence, of an eye of a patient, the video sequence being a plurality of video frames, determining a frequency spectrum from a pupillary data of the video sequence, and determining, based on the frequency spectrum, the physiological characteristic or drug of use of the patient. In an
(Continued)

embodiment, at least one frequency can be probed based on which physiological characteristic is being explored.

19 Claims, 6 Drawing Sheets

(51) Int. Cl.
*A61B 3/14* (2006.01)
*A61B 5/16* (2006.01)
*G16H 50/20* (2018.01)
*G16H 50/70* (2018.01)

(58) Field of Classification Search
CPC .......... A61B 5/0033; A61B 2010/0009; G16H 50/20; G16H 50/70
USPC .......................................................... 351/209
See application file for complete search history.

(56) References Cited

U.S. PATENT DOCUMENTS

| 2009/0161923 | A1 | 6/2009 | Kondo et al. | |
| 2011/0170064 | A1* | 7/2011 | Taylor ................... | A61B 3/0083 351/209 |
| 2011/0251468 | A1* | 10/2011 | Osorio ................... | A61B 5/165 607/45 |
| 2014/0268047 | A1* | 9/2014 | Hirsh ...................... | A61B 3/112 351/246 |
| 2016/0192837 | A1 | 7/2016 | Neice | |
| 2016/0381453 | A1* | 12/2016 | Ushakov ................. | H04M 1/05 381/71.6 |
| 2017/0100061 | A1 | 4/2017 | Finkel | |

FOREIGN PATENT DOCUMENTS

| CN | 106793942 | A | 5/2017 | |
| CN | 111918600 | A | 11/2020 | |
| JP | 2001-195594 | A | 7/2001 | |
| JP | 2006-326326 | A | 12/2006 | |
| JP | 2016-537152 | A | 12/2016 | |
| JP | 2017-529891 | A | 10/2017 | |
| WO | WO 2013/059656 | A2 | 4/2013 | |
| WO | WO-2013059656 | A2 * | 4/2013 | ............... A61B 3/09 |
| WO | WO 2015/042413 | A1 | 3/2015 | |
| WO | WO 2016/022414 | A1 | 2/2016 | |

OTHER PUBLICATIONS

Office Action dated Mar. 7, 2021 in corresponding Israeli Patent Application No. 275862, 2 pages.
Office Action dated Nov. 12, 2021 in corresponding Indian Patent Application No. 202017030155 (with English Translation), 7 pages.
International Search Report and Written Opinion dated Mar. 27, 2019 in PCT/US2019/013671 filed on Jan. 15, 2019.
Rosenberg et al., "Pupillary Hippus: an Unrecognized Example of Biologic Chaos", Journal of Biological Systems, 1999, vol. 7, No. 1, Retrieved from the Internet: <URL: https://www.researchgate.net/profile/Martin_Kroll2/publication263866809_Pupillary_hippus_An_unrecognized_example_of_ biologic_chaos/links/565ce9ac08ae4988a7bb8e57/Pupillary-hippus-An-unrecognized-example-of-biologic-chaos.pdf> , pp. 85-94.
Extended European Search Report dated Oct. 14, 2021 in corresponding European Patent Application No. 19740728.1, 9 pages.
Israeli Office Action dated Jul. 17, 2023 in Israeli Patent Application No. 275862 (with English translation) 13 pages.
Office Action dated Jan. 9, 2024, issued in counterpart KR Application No. 10-2020-7023416 filed Aug. 13, 2020, with English machine translation. (24 pages).
Examination Report dated Nov. 2, 2023, in Australian Patent Application No. 2019209323, citing document 24, therein, 5 pages.
Bokoch et al., "Fentanyl, an agonist at the mu opioid receptor, depresses pupillary unrest"—Autonomic Neuroscience: Basic and Clinical 189 (2015) 68-74 (abstract only).
Office Action dated Nov. 3, 2023 in Chinese Application No. 201980013097.0, along with an English translation.

* cited by examiner

BIOASSAY FOR THE NON-INVASIVE DETECTION OF DRUG USE AND PHYSIOLOGIC CONDITIONS

CROSS-REFERENCE TO RELATED APPLICATIONS

The present application claims priority to U.S. Provisional Application No. 62/619,434, filed Jan. 19, 2018, the teaching of which is hereby incorporated by reference in its entirety for all purposes. This application is further related to U.S. Patent Application No. 2015/0116665, filed Sep. 19, 2014, U.S. Patent Application No. 2017/0100061, filed Oct. 11, 2016, and U.S. Pat. No. 9,326,725, filed Mar. 30, 2011, the contents of which are incorporated herein by reference.

BACKGROUND

Field of the Disclosure

The present disclosure is related to drug use and/or physiologic impairments and their impact on pupillary hippus. Specifically, the present disclosure describes the utilization pupillometry for the detection of the drug use and/or physiologic impairments.

Description of the Related Art

Pupillary control requires a complex physiology involving numerous neuronal pathways. Pupillary behavior, therefore, provides a window to the integrity and functionality of these neuronal pathways. Furthermore, pupillary behavior, as indicated by contraction and dilation of the iris by the sphincter and dilator muscles, can reflect alterations or abnormalities in the metabolism or the structure of the central nervous system. This connection to the central nervous system makes the determination and identification of pathologies critical in clinical and experimental settings, and suggests that evaluation of pupillary behavior may provide a mechanism for rapid detection and diagnosis of pathologies.

Pupil assessment, however, while being a routine practice in medical care and used in a variety of settings ranging from first responders to intensive care units, is most commonly performed using a penlight and visual, subjective observation. This subjective approach is hindered by inter-operator variability attributed to operator expertise and, though an easy assessment method, fails to provide granular data. For instance, the information generated by the penlight approach can be limited to gross pupil features such as the presence or absence of light reflex and a rough estimation of pupil size and symmetry. As would be expected, subtle changes that may be important tools in tracking clinical conditions such as brain trauma or viability following cardiac or pulmonary arrest cannot be assessed.

Even when more resolved methods have been employed, such as pupillometers, broad acceptance and deployment has been slow. These methods, though they can be used to evaluate pupillary size and reactivity, can be costly and can require stand-alone equipment that provides raw data without interpretation, necessitating the introduction of a trained professional to evaluate the data, synthesize the information, and provide proper guidance to a consumer regarding appropriate interventions.

Therefore, effective and convenient evaluation of pupillary behavior, promising to provide pupillary measurements that can be used to, among other things, monitor drug use, drug abuse, drug tolerance, and opioid hyperalgesia, is needed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

According to an embodiment, the present disclosure is related to an apparatus for evaluation of a pupillary hippus of a patient.

In an embodiment, the present disclosure is related to an apparatus for evaluation of a pupillary hippus of a patient, comprising a display, and processing circuitry configured to transform experimental data of the pupillary hippus of the patient and reference data via frequency-based transformation, calculate a first parameter of one or more selected parameters based upon the transformed experimental data of the pupillary hippus of the patient, calculate, based upon the transformed reference data, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on the display and based upon the determination, the evaluation of the pupillary hippus of the patient, wherein the evaluation of the pupillary hippus of the patient is an identification of an opioid as the biologically-active target.

In an embodiment, the present disclosure is further related to an apparatus for evaluation of a pupillary hippus of a patient, comprising a display, and processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on the display and based upon the determination, the evaluation of the pupillary hippus of the patient.

In an embodiment, the present disclosure is further related to an apparatus for evaluation of a pupillary hippus of a patient, comprising processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on a display and based upon the determination, the evaluation of the pupillary hippus of the patient.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

According to an embodiment, the present disclosure describes a method and apparatus that allows clinicians, health care professionals, and consumers, in cases, to evaluate, precisely and objectively, the dynamic pupillary oscillations that, in part, define pupillary behavior. Moreover, these dynamic pupillary oscillations can be used in conjunction with a variety of pathology-specific algorithms, the pathology-specific algorithms being specific to different drug signatures and physiologic conditions, in order to identify pathologies therefrom. In an embodiment, the pathology-specific algorithms can be directed to, among others, alcohol, opioids, cannabinols, alpha-2 agonists, benzodiazepines, ketaminemorphine, morphine-3-glucuronide, morphine-6-glucuronide, or a combination thereof.

According to an exemplary embodiment of the present disclosure, evaluation of dynamic pupillary oscillations can be performed by an apparatus, or a pupillometry device, that combines an imaging apparatus having an imaging sensor, such as an infrared camera or CMOS sensor within housing, and a display apparatus which can be a smartphone or a dedicated display module. In an embodiment, the imaging apparatus and the display apparatus may be both contained within a smartphone or similar mobile terminal. Connection with the display will enable a software application to objectively generate comparative information of the dynamic pupillary oscillations such that it can facilitate understanding of the comparative information. To this end, the above-described apparatus can be a screening tool and software applications thereof can be algorithms and methods developed to specifically address a variety of clinical situations. These software applications enable objective measurement of the dynamic pupillary behavior in, for example, the clinical setting and can be stored within a memory of the smartphone or the apparatus.

According to an embodiment, the above-described apparatus of the present disclosure can implement a method in combination with additionally-described hardware. For example, such hardware can be a chamber constructed to adapt a smartphone to a patient's, or a user's, face. To facilitate data acquisition, the exemplary imaging apparatus, or infrared camera, can be adaptable, via the additionally-described hardware, to ergonomically form to a patient's face to enable accurate pupil assessment. Moreover, this allows implementation of the method in myriad environments, wherein it can be performed by a ubiquitous device. The method, in an embodiment, can be performed by processing circuitry configured to control the imaging apparatus of the smartphone or other device in order to acquire video sequences of an eye of a person. Such video sequences can be acquired, for example, at 100 frames per second, though it should be appreciated that other frame rates can be used in order to obtain the pupillary video sequences.

During real-world implementation, the above-described apparatus and method thereof, according to an exemplary embodiment, can provide rapid access to patient data that can be important tools in a variety of clinical situations. By comprising an integration-ready chamber that is adjustable to a patient's face with a dedicated display for the collected information, in an embodiment, convenient and mobile acquisition of patient pupillary data can be realized and analysis expediently performed. Enhancing the adaptability of the approach, specific algorithms can be deployed in order to interpret the acquired patient pupillary data, adjustable to different clinical situations, thereby allowing broad use and access by a variety of professionals and laypersons, including, but not limited to, medical professionals.

Among multiple applications, the assessment of pupillary oscillations can be applied to the identification of drug use. The identification of drug use presents one of the greatest opportunities for broader use of pupillometry. Drugs confer specific effects on the autonomic nervous system, thereby affecting the pupil, and pupillary oscillations, directly. Examination of pupillary oscillations, known as hippus, using spectral analysis, for example, renders specific, attributable frequency responses. Drug usage changes the spectral profile of hippus in specific, attributable ways. The apparatus and method of the present disclosure, as introduced above, may be an important tool in understanding drug usage correlations and evaluating patients for drug use status.

Additionally, and according to an embodiment, the apparatus and method of the present disclosure may be employed in the evaluation of the function of the autonomic nervous system in the context of a physiologic condition. Pupillary oscillations are known to vary due to abnormal activity in the autonomic nervous system, such as the presence of a dysautonomia. Therefore, the function of the autonomic nervous system and abnormal activities thereof may be evaluated via the apparatus and method of the present disclosure, thus render the present disclosure an important tool in evaluating patients for the presence of specific physiologic conditions.

With reference now to the Figures and as described above, the present disclosure, according to an embodiment, is related to an apparatus, and a method thereof, of determining the presence of a biologically-active compound, a drug, or a physiologic perturbation in a patient. Briefly, the method includes, for instance, the steps of: (1) acquiring a video sequence of an eye of a patient, the video sequence including a plurality of video frames, (2) detecting and measuring pupil dimensions in each of the plurality of video frames of the video sequence, wherein the dimensions of the time-based pupil size form pupillary oscillations of the patient, (3) determine, using local or remote processing circuitry, based upon the pupillary oscillations, a frequency spectrum of the detected and measured pupil dimensions over time, and (4) determining, using the processing circuitry and based upon a band power of the frequency spectrum (i.e. area under the curve), the presence of a drug or a physiologic condition of the patient.

Figure 1:
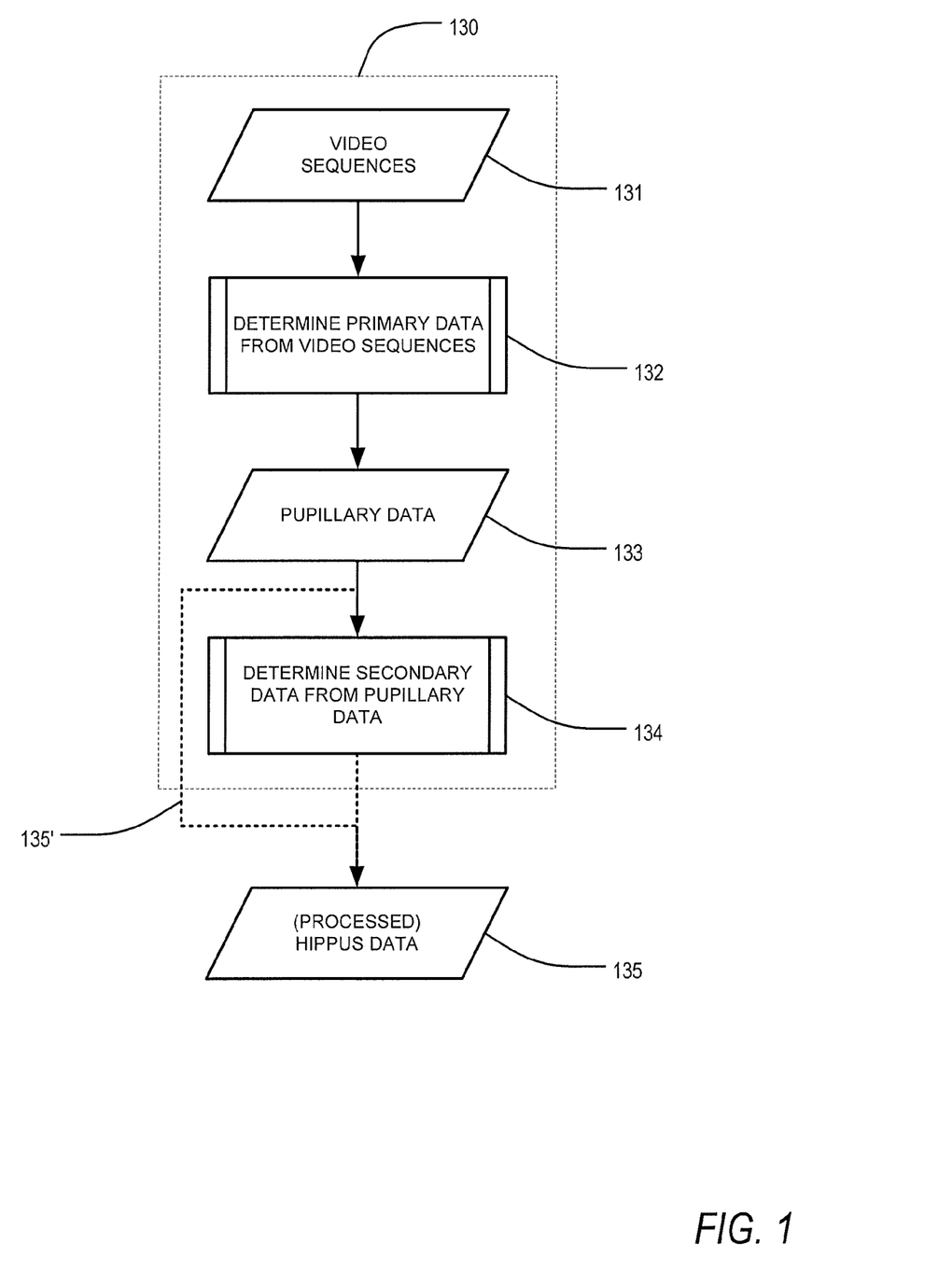
FIG. 1 is a flow diagram describing processing of acquired data, according to an exemplary embodiment of the present disclosure.

Referring now to FIG. 1, and with additional details as to the above, the method can comprise data processing 130 that includes first, as outlined in FIG. 1, the acquisition of a video sequence 131 of an eye of a patient, the video including a plurality of video frames. Following acquisition 131, primary data such as, for instance, pupillary dimensions and pupillary oscillations therefrom, can be determined for each of the plurality of video frames in the video sequence of the eye of the patient 132.

Figure 2:
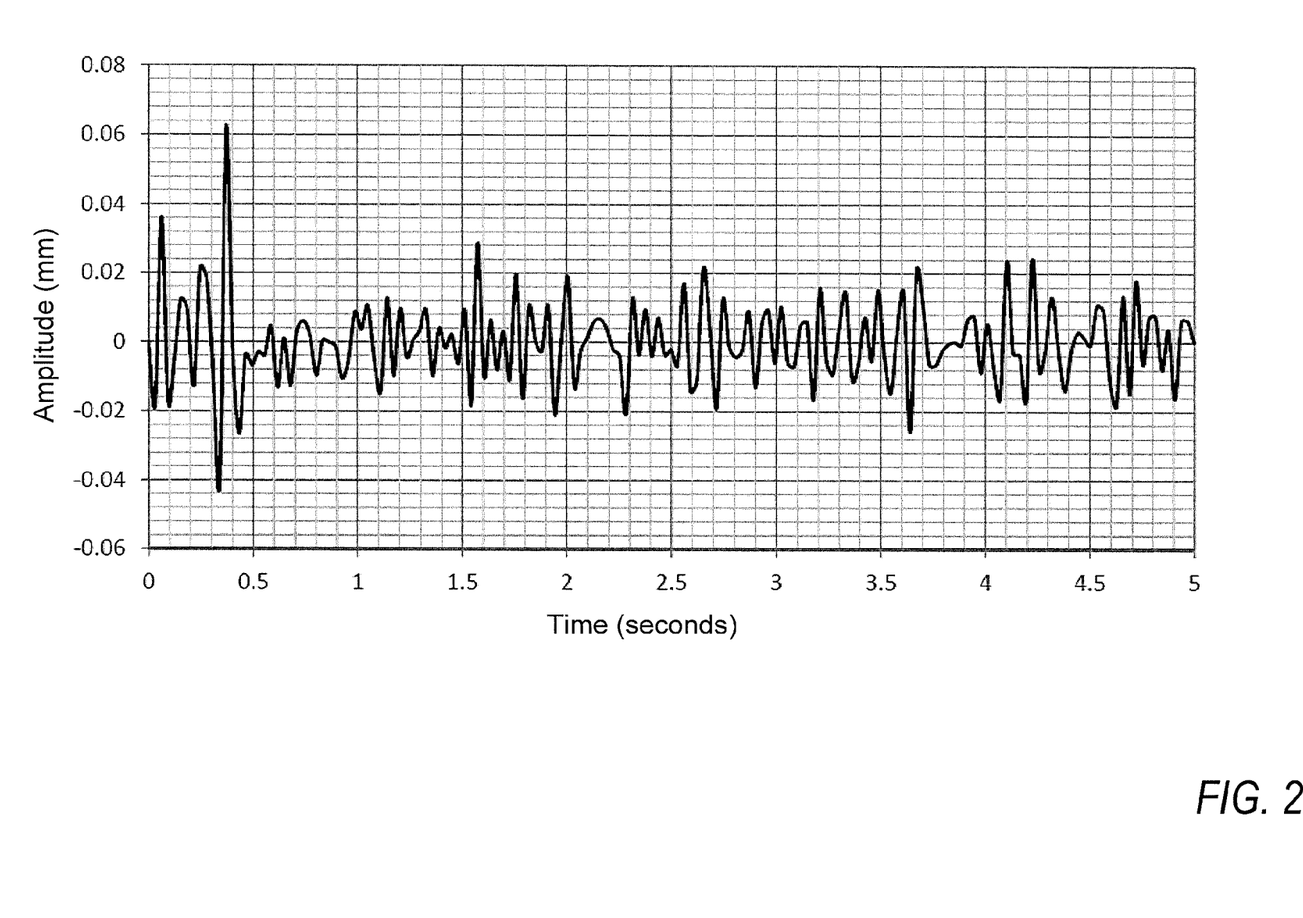
FIG. 2 is a graphical representation of pupillary oscillations as isolated prior to spectral analysis, according to an exemplary embodiment of the present disclosure.

According to an embodiment, FIG. 2 is a graphical illustration of pupillary data of an isolated hippus isolated prior to spectral analysis. Specifically, amplitude pupillary oscillations over a 5-second period of a pupillary light reflex of are shown.

Returning now to FIG. 1, the data 133 that defines the pupillary oscillations can then be mined, via processing circuitry either local or remote, to determine, for instance, secondary data 134 that can include a frequency spectrum of the pupillary oscillations over time. The frequency spectrum determined to be secondary data 134 of the pupillary data 133 can then be provided as processed hippus data 135 to a method of the present disclosure for evaluating the newly processed data. Alternatively, or in combination with, the pupillary data can forgo additional data manipulation 135' and can immediately define processed hippus data 134.

With regard to implementation of the method of the present disclosure, the processed hippus data 134 can be accessible during run time of the method, wherein the processed hippus data 134 from an experimental hippus and processed hippus data 134 from a reference hippus can be used to determine the presence of, among others, a biologically-active compound, a drug, or other physiologic perturbation of the patient. For instance, this can be a determination of the presence and/or level of alcohol-induced impairment based on a band power calculated from the frequency spectrum.

Different applications, such as detection of drug use or detection of a medical condition or physical perturbation, can take into account different pupillometric measures and different amounts of weight or different ways of processing the pupillometric measures.

The method of FIG. 1 can be initiated by, for example, (1) during the initial processing of the video sequences 132, localizing, in a first frame among the plurality of frames, a center of the pupil and two points on a boundary of the pupil and the iris, (2) generating, using the processing circuitry, a mask image corresponding to an expected location of the iris based on said localizing, said mask image including a plurality of pixels, and (3) determining the pupillary dimensions (i.e. primary data), and pupillary oscillations therefrom, based on the generated mask image.

The acquired video sequence can be processed, as above, by a processor in an attachable device such as, among others, a smartphone or cloud based processing. Although a smartphone, in context of the processing circuitry above, is described herein and has been described previously, as evidenced by US 2015/0116665 A1 and incorporated herein by reference, it can be appreciated that any processor, including an external processor or cloud-based processing circuitry, can be used to process the acquired video sequence.

Further to the above, the acquired video sequence can include pupillary reaction to, for instance, a flash of light. In order to create this reaction, or pupillary light reflex, a flash of light, according to standardized lighting conditions, can be provided by the flashlight of the aforementioned smartphone or similar mobile device.

Pupillary oscillations and/or reactions to light, as described above, can reflect the activity of the autonomic nervous system. For instance, in exhibiting the pupillary light reflex and reflecting the integrity of the autonomic nervous system, constriction, or miosis, occurs in response to the flash of light as a result of increased parasympathetic tone while dilation, or mydriasis, reflects increased sympathetic tone. The pupillary light reflex can be evaluated via the method, and apparatus thereof, of the present disclosure, wherein higher frequency activation occurs with increased sympathetic tone and lower frequency activation occurs from increased parasympathetic tone. Applied in the real world, pupillary oscillations may be impacted by the activity of certain biologically-active compounds, drugs, of physiological conditions that interact with receptors of the autonomic nervous system, impacting either sympathetic or parasympathetic responses.

According to an embodiment, a variety of pupillometric measures can be evaluated from pupillary data following initial video sequence processing 132 such that, in combination with secondary data 134 including frequency spectra, patient response profiles can be better characterized. There are at least six pupillometric measures used in the generation of algorithms that can aid in the determination of a physiological characteristic such as, for example, usage of drugs or a medical condition. At least two of the pupillometric measures are static measures and can include baseline pupil size and maximally constricted size. These measures can be used to generate, for example, constriction amplitude. As introduced above, the baseline pupil size can be found before the flash of light and the maximally constricted size can be determined after the flash of light. At least four of the pupillometric measures can be dynamic measures and can be dynamic responses to the flash of light, including velocity of constriction (average constriction velocity and maximum constriction velocity), latency of constriction, and velocity of re-dilation. As related to the detection and identification of drug use or pathologic condition, the various parameters of the pupillary light reflex are impacted in a predictable way by various drugs and medical conditions. Any of the at least six pupillometric measures can be suitable metrics according to the application of the measurement. As the application changes, such as the detection of specific drug use or detection of a specific medical condition, different pupillometric measures and different amounts of weight or different ways of processing in pupillometric measures can be considered, as appropriate.

According to an embodiment, the above-described pupillometric measures, or parameters, can include at least one of a plurality of additional parameters including a maximum pupil size, a maximum change in size of the pupil, a maximum velocity of re-dilation of the pupil, a mean velocity of re-dilation of the pupil, a maximum area of the pupil, a minimum area of the pupil, a mean area of the pupil, the time to 75% recovery of pupil size, the time to 100% recovery of pupil size, and the area under the curve of the pupillary light reflex.

According to an embodiment, the secondary data 134 can include, for instance, a frequency spectrum. The frequency spectrum can be derived from the pupillary data via frequency-based transform methods. Such frequency-based transform methods may be a fast Fourier transform, Hilbert Huang transform, and the like, as would be understood by one of ordinary skill in the art. From the frequency spectrum, parameters such as an amplitude at a specific frequency or a band power across a range of frequencies, wherein the specific frequency or range of frequencies are correlated with a level of activity of a pathology, can be determined. Moreover, the frequency spectrum may be evaluated write large, wherein a mathematical model of the frequency spectrum is correlated with a level of activity of a pathology. To this end, heuristic models can be used in the development of algorithms.

Figure 3:
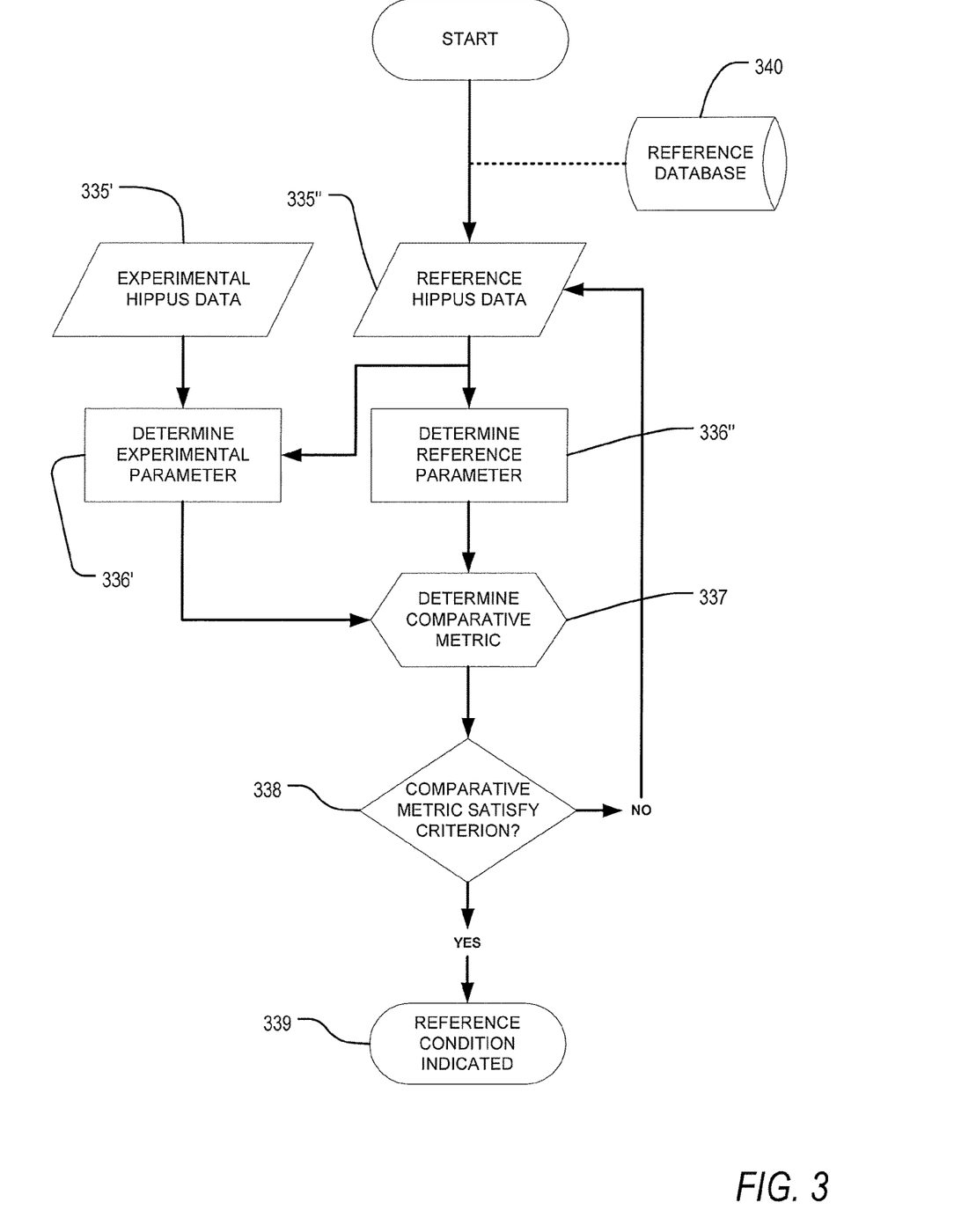
FIG. 3 is a flow diagram describing evaluation of a spectral analysis, according to an exemplary embodiment of the present disclosure.

During implementation of the above-described methods, and referring now to FIG. 3, selected parameters can be determined for experimental and reference data and compared such that the presence and/or quantity of a substance, drug, or physiologic substance can be determined.

To this end, first, reference hippus data 335" can be acquired from a reference database 340 and experimental hippus data 335' can be acquired, for example, from a current patient. This hippus data is analogous to the processed hippus data of FIG. 1, wherein the method of FIG. 1 has been applied to an acquired video sequence.

Having acquired appropriate hippus data, a first parameter, or experimental parameter 336', can be determined from the experimental hippus data 335' of a pupillary hippus of the patient. The experimental parameter 336' can be, but is not limited to, amplitude, frequency, band power, and a mathematical model of the waveform, as described above. Additionally, the experimental parameter 336' can be, among others, baseline pupil size, maximum pupil size, minimum pupil size, velocity of constriction (average constriction velocity and maximum constriction velocity), latency of constriction, velocity of re-dilation, maximum change in size of the pupil, maximum velocity of re-dilation of the pupil, mean velocity of re-dilation of the pupil, maximum area of the pupil, minimum area of the pupil, mean area of the pupil, time to 75% recovery of pupil size, time to 100% recovery of pupil size, and area under the curve of the pupillary light reflex.

Similarly to the above, a first parameter, or reference parameter 336", can be determined from reference hippus data 335" of a pupillary hippus of a reference patient or a representative pupillary hippus of a population of patients. The reference parameter 336" can be, but is not limited to, amplitude, frequency, band power, and a mathematical model of the waveform, as described above. Additionally, the experimental parameter 336' can be, among others, baseline pupil size, maximum pupil size, minimum pupil size, velocity of constriction (average constriction velocity and maximum constriction velocity), latency of constriction, velocity of re-dilation, maximum change in size of the pupil, maximum velocity of re-dilation of the pupil, mean velocity of re-dilation of the pupil, maximum area of the pupil, minimum area of the pupil, mean area of the pupil, time to 75% recovery of pupil size, time to 100% recovery of pupil size, and area under the curve of the pupillary light reflex.

In an exemplary embodiment, a second parameter, or comparative metric 337, can be determined as a computation based upon the experimental parameter 337' and the reference parameter 337" determined from the pupillary hippus of the patient and the pupillary hippus of the reference patient, for example, respectively. The comparative metric can include, among others, delta band power, or the difference between the band power of the experimental data and a corresponding band power of the reference data, % delta band power, normalized delta band power, and a similarity ratio between mathematical models of the experimental data and the reference data.

In an embodiment, the comparative metric 337 can be a correlation of an experimental waveform and a reference waveform, wherein a lack of correlation of the respective waveforms can be indicative or not of a physiologic condition.

Following determination of the comparative metric 337, according to an embodiment, the comparative metric 337 can be evaluated 338 with respect to a pre-determined threshold to determine the presence or absence of a biologically-active substance, a drug, or a physiologic perturbation. The biologically-active substance, the drug, or the physiologic perturbation, as defined by the comparative metric evaluated, can be indicated via a display.

For example, a patient may be suspected of recreational use of opioids or, in particular, methadone. If delta band power is the comparative metric and, over a frequency range associated with methadone users, is determined to be significantly large when comparing the patient's data with reference data of a comparable patient, it can be determined that the patient has had an acute exposure to methadone. In another example, a patient may be suspected of over use of a prescribed opioid such as hydrocodone. If delta band power, over a frequency range associated with hydrocodone use, is determined to be significantly large when comparing the patient's data with reference data from an expected hydrocodone band power user, it can be determined that the patient has had an acute overexposure to hydrocodone.

According to an embodiment, following the evaluation of the comparative metric with respect to a selected criterion 338, the outcome or, physiologic condition, can be displayed 339 via a display of the device described with reference to FIG. 7 such that a user can be alerted of the patient's condition, normal or otherwise.

Evaluation of the comparative metric relative to a criterion may reflect analysis of patterns and correlations of quantified frequency spectra that may be predictive of particular scenarios. The patterns and correlations may further predictive of interactions of drugs and their impact on pupillary hippus. According to an embodiment, these patterns and correlations can be identified by comparison against a library of frequency spectra associated with specific biologically-active compounds or drugs, a panel of specific biologically-active compounds or drugs, or multiple, interacting biologically-active compounds or drugs.

As discussed with respect to FIG. 3, comparisons of unknown, or experimental data, and reference data can be conducted by evaluating, for example, amplitudes at one or more, or a set of, specific frequencies along the frequency domain.

Figure 4:
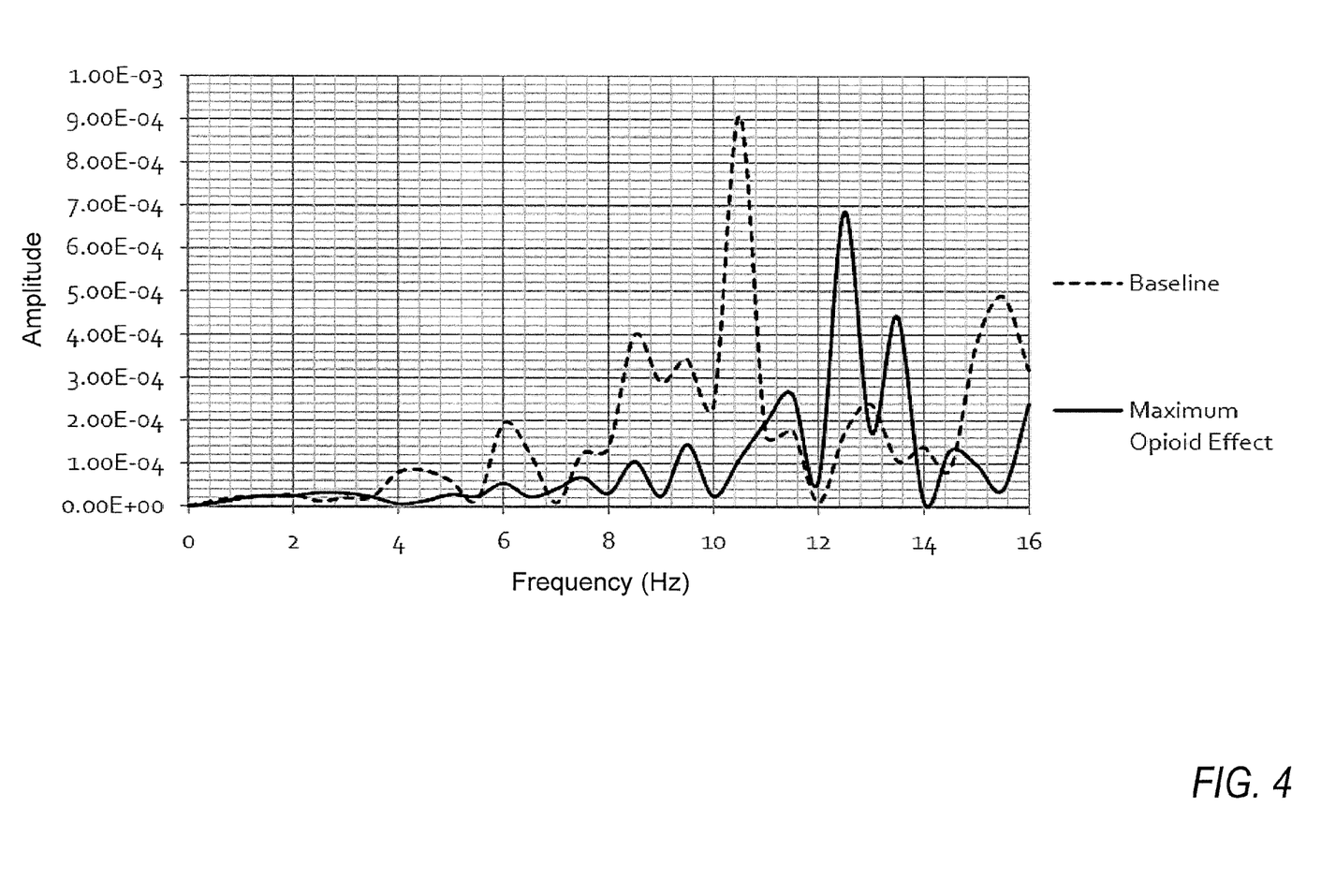
FIG. 4 is a graphical representation of evaluation of a pupillary light reflex after exposure to opioids, according to an exemplary embodiment of the present disclosure.

Accordingly, FIG. 4 provides a graphical representation of a spectral evaluation of experimental hippus data and reference hippus data, as would be performed during the generation of secondary data in FIG. 1. As shown, experimental hippus data, captured at a time period of 'maximum opioid effect' is illustrated alongside reference data displayed as a 'baseline'. The impact of opioid use can be observed at varying frequencies across a spectrum for a single patient and attendant analysis of parasympathetic and sympathetic actions can be inferred therefrom. As observed in FIG. 4, for instance, opioid use modifies pupillary oscillations between 8 Hz and 11 Hz, as compared with baseline, and high frequency pupillary oscillations between 12 Hz and 14 Hz. Such modifications may be indicative, in the case of high frequency pupillary oscillations, increased sympathetic tone in response to opioid exposure. In an example, the identification of physiologic perturbations could be performed by evaluation of a correlation between mathematical models of the plotted data.

Figure 5:
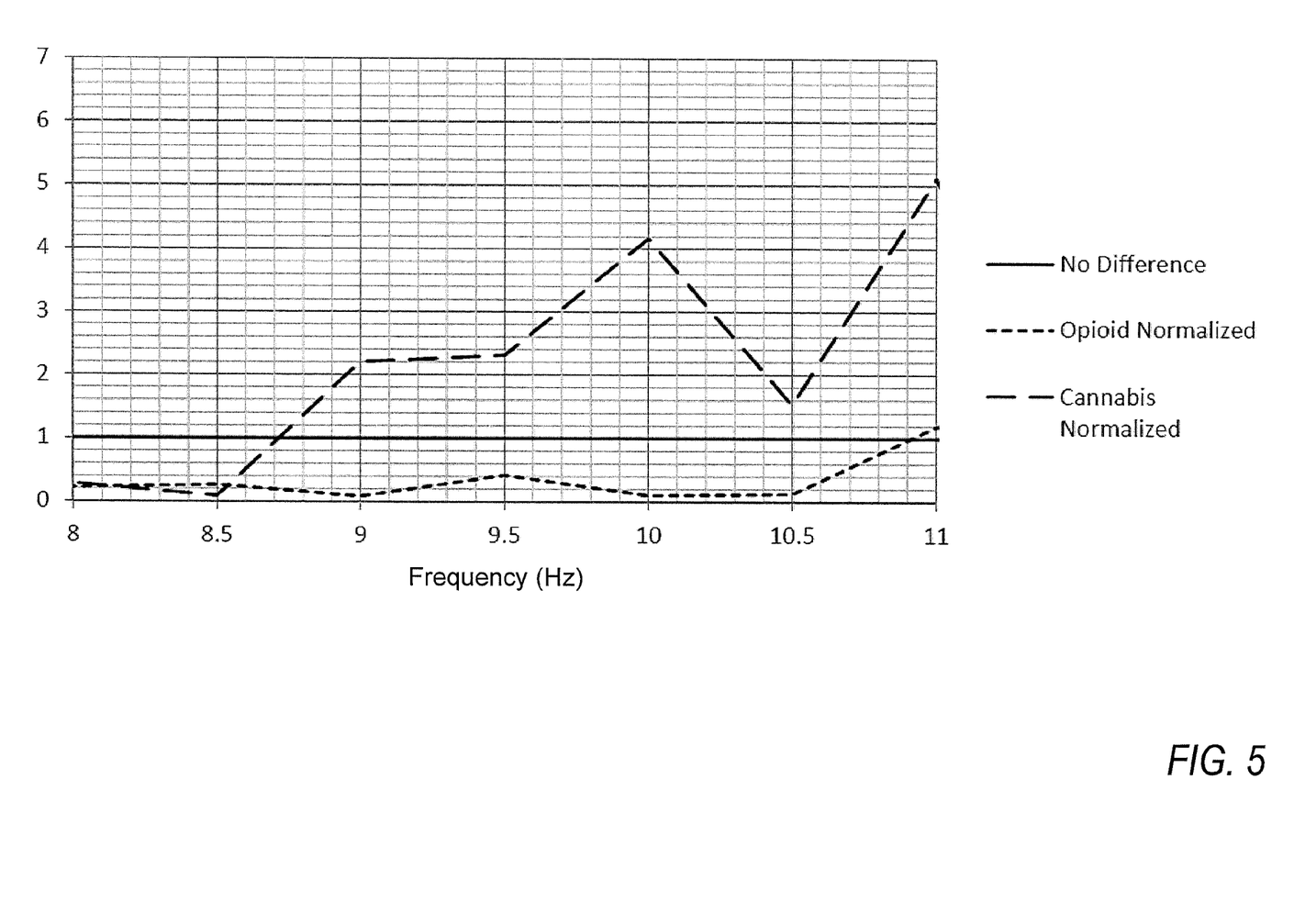
FIG. 5 is a graphical representation of transform data of maximal drug effect normalized to baseline for a plurality of drugs, according to an exemplary embodiment of the present disclosure.

The specificity suggested in FIG. 4 is displayed in FIG. 5 with regards to a plurality of drugs, wherein fast Fourier transform data of the hippus of a patient using opioids and a patient using *cannabis* normalized to baseline is presented. As can be observed, the change in amplitude of each patient is varied relative to baseline over a frequency range of 8 Hz to 11 Hz, where *cannabis* use may increase sympathetic tone, for example, and opioid use may decrease sympathetic tone, relative to baseline.

According to an embodiment, experimental hippus data containing unknown frequency spectra may be analyzed, or filtered, with respect to a specific target biologically-active compound. This analysis, or filtering, can be based upon prior investigations of the biologically-active target compound. Filtering may include removal of data above, below, or within a predetermined frequency, and the removal of data above, below, or at predetermined amplitude, for example, wherein the predetermined frequency and the predetermined amplitude are correlated with the specific target biologically-active compound. For instance, it may be known that an opioid may have increased amplitude oscillations between 12 Hz and 14 Hz along the frequency domain, as shown in FIG. 4. Through determination of the area under the curve between these two frequencies, the area under the curve being referred to as a band power, the unknown frequency spectra data may be compared to reference frequency spectra data of a known entity to determine a delta band power. The delta band power, as discussed with respect to FIG. 3, can be a comparative metric or second parameter and, if present, the delta band power may be above a pre-determined threshold according to the sensitivity of the data acquisition equipment.

Furthermore, comparisons of complete, longitudinal pupillary responses, in the frequency domain, can be compared to a library of frequency spectra via pattern recognition techniques employed in machine learning for determining irregularities in data. This approach can identify, for example, one or more amplitude inflection points in the frequency domain that correlate to one or more known biologically-active compounds, drugs, or physiologic conditions.

Complementary to the above approaches, and as suggested, each unknown frequency spectra can be analyzed with respect to the effects of multiple, interacting biologically-active compounds, providing context to the impact of drug-drug interactions on the nervous system. For example, an unknown frequency spectra data may be filtered in the targeted context of the pupillary effects of the interaction of alcohol and opioids in order to isolate said compounds.

Moreover, in an embodiment, each unknown frequency spectra can be compared against a library of reference hippus data and it may be determined that one or more drug-drug interactions can be correlated with physical perturbations of the pupillary light reflex.

For instance, the method can be applied such that, separately, alcohol use is evaluated in one instance and opioid use is evaluated in a second instance. In a third instance, the impact of combined alcohol use and opioid use can be evaluated. Clinically-significant frequency ranges, or bands, such as 0.3 Hz-3.0 Hz or 3.1 Hz-5.0 Hz, for example, can be evaluated to probe for specific biologically-active compounds, drugs, and the like, wherein one indicates alcohol presence and the other indicates opioid use. In the case wherein the combination of alcohol and opioids modifies the impact that either would impart separately, a filter can be applied to eliminate one from the frequency spectra such that the other may be detected and quantified. This can be a common occurrence in real world applications, wherein a first compound of a group of compounds may substantially outcompete the group for access to a specific receptor, thereby subduing the effect of competing compounds, masking the presence of other compounds of the group, and modifying the pupillary light reflex writ large.

Moreover, the band power determined at each of these frequency bands can indicate, when calibrated, a concentration of a biologically-active substance or drug, thereby providing a potentially powerful, non-invasive tool for drug usage detection and monitoring.

According to an embodiment, experimental hippus data containing unknown frequency spectra may be compared each every entry of the reference hippus data of the reference database in order to identify the unknown affecter of the frequency spectra. For example, one or more drugs may have an influence on a frequency spectrum of data from an experimental hippus. This frequency spectrum can be compared against a reference database, containing frequency spectra being impacted by a plurality of drugs, such that the presence and, if possible, identity of the one or more drugs of the experimental hippus can be determined. Importantly, this approach, while more computationally intensive, does not require a user to have a prediction of the one or more drugs of the frequency spectrum of the experimental hippus and, instead, allows for comparison of the unknown spectrum against a panel of possible drug candidates.

According to an embodiment, unknown and quantified frequency spectra data can be evaluated ad hoc to detect the presence of a biologically-active compound, as compared to a baseline. This approach may be useful when merely the presence of a specific biologically-active compound is in question. In an embodiment, the baseline can be established from a library a reference data of a variety of control patients, a prior control dataset of the same patient, or a combination thereof.

Further to the above, according to an embodiment, the present method can be used to detect dysautonomias, which include a variety of conditions including diabetic neuropathy and postural orthostatic tachycardia syndrome.

The method of the present embodiments can also be used for management of drug use and monitoring thereof. Currently, drug dose management is subjective according to clinician judgment. The approach of the present disclosure can be applied to long-term or repeated drug monitoring, including the detection of biologically-active compounds and respective, subsequent metabolites. Drug use and impairment with time, including dose response effects, can be observed per this method. Metrics determined therein can be used clinically for objective analyses.

Moreover, the method can be developed to work as triage test in drivers suspected to be under the influence of alcohol or controlled substances. If there are any spectra unique to illegal substances discovered during the test, the driver will be submitted to other tests.

In addition to the above, the method of the present embodiments can be further implemented for the monitoring of post-surgery sedation of surgical patients.

According to an embodiment, the method of the present embodiments can also be used to discriminate between direct drug effects on the pupil vs. analgesic impact, (i.e., the method allows for the discrimination of drug vs. system-dependent parameters by using elements of static or dynamic pupil parameters as analogues of pharmacokinetics and area under the curve of the pupillary reflex dilation as the analogue of analgesic pharmacodynamics. The fast Fourier transform-derived "signature" of the present disclosure provides a non-invasive approach for further informing this paradigm by indicating the presence of a substance.

In an embodiment, the method of the present disclosure can be used in the context of analgesic response or other drug effects when combined with other features of the pupillary response including, but not limited to, the pupillary light reflex and the neurospecific neurostimulus-induced pupillary light reflex. This approach allows for isolation of drug-induced hyperalgesia, or a state of exposure-mediated nociceptive sensitization, from increased pain sensitivity resulting from injury or disease progression.

Figure 6:
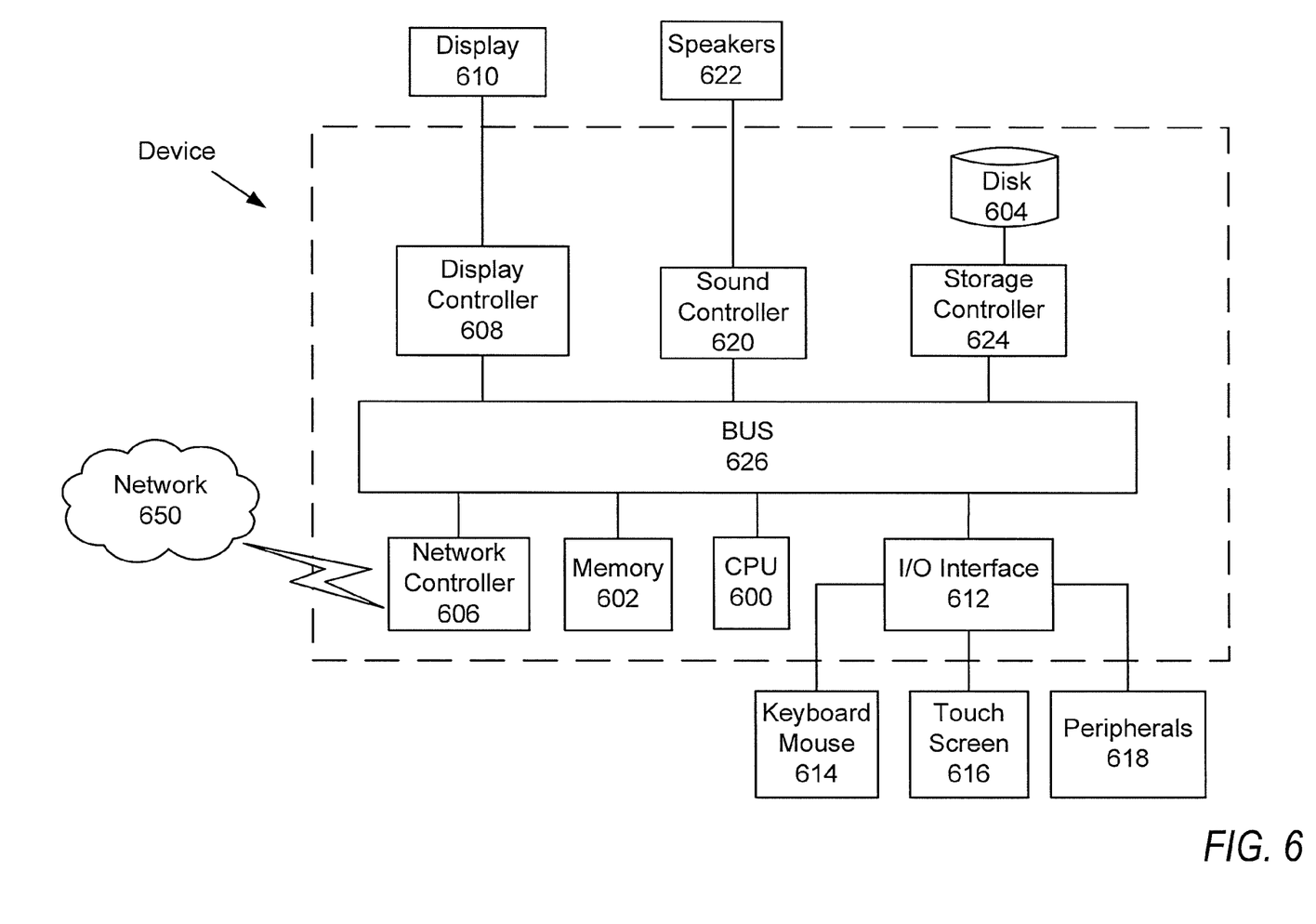
FIG. 6 is a hardware description of an apparatus, according to an exemplary embodiment of the present disclosure.

Next, a hardware description of an apparatus, or device, according to exemplary embodiments is described with reference to FIG. 6. In FIG. 6, the device includes a CPU 600 which performs the processes described above. The process data and instructions may be stored in memory 602. These processes and instructions may also be stored on a storage medium disk 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the device communicates, such as a server or computer.

Further, the claimed advancements may be provided as a utility application, background daemon, or component of an operating system, or combination thereof, executing in conjunction with CPU 600 and an operating system such as Microsoft Windows 7, UNIX, Solaris, LINUX, Apple MAC-OS and other systems known to those skilled in the art.

The hardware elements in order to achieve the device may be realized by various circuitry elements, known to those skilled in the art. For example, CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the inventive processes described above.

The device in FIG. 6 also includes a network controller 606, such as an Intel Ethernet PRO network interface card from Intel Corporation of America, for interfacing with network 650. As can be appreciated, the network 650 can be a public network, such as the Internet, or a private network such as an LAN or WAN network, or any combination thereof and can also include PSTN or ISDN sub-networks. The network 650 can also be wired, such as an Ethernet network, or can be wireless such as a cellular network including EDGE, 3G and 4G wireless cellular systems. The wireless network can also be WiFi, Bluetooth, or any other wireless form of communication that is known.

The device further includes a display controller 608, such as a NVIDIA GeForce GTX or Quadro graphics adaptor from NVIDIA Corporation of America for interfacing with display 610, such as a Hewlett Packard HPL2445w LCD monitor. A general purpose I/O interface 612 interfaces with a keyboard and/or mouse 614 as well as a touch screen panel 616 on or separate from display 610. General purpose I/O interface also connects to a variety of peripherals 618 including printers and scanners, such as an OfficeJet or DeskJet from Hewlett Packard.

A sound controller 620 is also provided in the device, such as Sound Blaster X-Fi Titanium from Creative, to interface with speakers/microphone 622 thereby providing sounds and/or music.

The general purpose storage controller 624 connects the storage medium disk 604 with communication bus 626, which may be an ISA, EISA, VESA, PCI, or similar, for interconnecting all of the components of the device. A description of the general features and functionality of the display 610, keyboard and/or mouse 614, as well as the display controller 608, storage controller 624, network controller 606, sound controller 620, and general purpose I/O interface 612 is omitted herein for brevity as these features are known.

Embodiments of the present disclosure may also be as set forth in the following parentheticals.

(1) An apparatus for evaluation of a pupillary hippus of a patient, comprising a display, and processing circuitry configured to transform experimental data of the pupillary hippus of the patient and reference data via frequency-based transformation, calculate a first parameter of one or more selected parameters based upon the transformed experimental data of the pupillary hippus of the patient, calculate, based upon the transformed reference data, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on the display and based upon the determination, the evaluation of the pupillary hippus of the patient, wherein the evaluation of the pupillary hippus of the patient is an identification of an opioid as the biologically-active target.

(2) The apparatus according to (1), wherein the processing circuitry is further configured to determine whether the generated metric achieves the predetermined threshold based upon a correlation between the first parameter of the experimental data and the corresponding first parameter of the reference data.

(3) The apparatus according to either (1) or (2), wherein the first parameter based upon the experimental data is an amplitude at a predetermined frequency.

(4) The apparatus according to any of (1) to (3), wherein the first parameter based upon the experimental data is band power.

(5) The apparatus according to any of (1) to (4), wherein the generated metric is a difference between a band power of the experimental data and a band power of the reference data.

(6) The apparatus according to any of (1) to (5), wherein the first parameter based upon the experimental data is a mathematical model of the experimental data.

(7) The apparatus according to any of (1) to (6), wherein the first parameter based upon the experimental data is a mathematical model of a frequency spectrum of the experimental data.

(8) The apparatus according to any of (1) to (7), wherein the generated metric is a similarity ratio of mathematical models of a frequency spectrum of the experimental data and of the reference data.

(9) The apparatus according to any of (1) to (8), wherein the processing circuitry is further configured to acquire a plurality of video sequences of an eye of the patient, generate pupillary data based upon primary data calculated from the plurality of video sequences, the primary data including time-based pupillary dimensions, and calculate, from the generated pupillary data, secondary data, wherein the secondary data include the frequency spectrum of the pupillary hippus.

(10) The apparatus according to any of (1) to (9), wherein the primary data are calculated based upon a mask image, the processing circuitry, in order to generate the mask image, being further configured to locate a center of a pupil of the eye, a boundary of the pupil of the eye, and an iris of the eye, and generate the mask image, the mask image corresponding to an expected location of the iris based upon the location of the center of the pupil of the eye, the boundary of the pupil of the eye, and the iris of the eye.

(11) An apparatus for evaluation of a pupillary hippus of a patient, comprising a display, and processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on the display and based upon the determination, the evaluation of the pupillary hippus of the patient.

(12) The apparatus according to (11), wherein the processing circuitry is further configured to determine whether the generated metric achieves the predetermined threshold based upon a correlation between the first parameter of the experimental data and the corresponding first parameter of the reference data.

(13) The apparatus according to either of (11) or (12), wherein the processing circuitry is further configured to transform the experimental data of the pupillary hippus of the patient and the reference data via frequency-based transformation, and the generated metric is a difference between a band power of the experimental data and a band power of the reference data.

(14) The apparatus according to any of (11) to (13), wherein the processing circuitry is further configured to transform the experimental data of the pupillary hippus of the patient and the reference data via frequency-based transformation, and the generated metric is a similarity ratio of mathematical models of a frequency spectrum of the experimental data and of the reference data.

(15) The apparatus according to any of (11) to (14), wherein the processing circuitry is further configured to acquire a plurality of video sequences of an eye of the patient, generate pupillary data based upon primary data calculated from the plurality of video sequences, the primary data including time-based pupillary dimensions, and calculate, from the generated pupillary data, secondary data, wherein the secondary data include the frequency spectrum of the pupillary hippus.

(16) The apparatus according to any of (11) to (15), wherein the primary data are calculated based upon a mask image, the processing circuitry, in order to generate the mask image, being further configured to locate a center of a pupil of the eye, a boundary of the pupil of the eye, and an iris of the eye, and generate the mask image, the mask image corresponding to an expected location of the iris based upon the location of the center of the pupil of the eye, the boundary of the pupil of the eye, and the iris of the eye.

(17) The apparatus according to any of (11) to (16), wherein the evaluation of the pupillary hippus of the patient is an identification of the biologically-active target, the biologically-active target being selected from a group including alcohol, opioids, cannabinols, alpha-2 agonists, benzodiazepines, ketaminemorphine, morphine-3-glucuronide, morphine-6-glucuronide, or a combination thereof.

(18) The apparatus according to any of (11) to (17), wherein the processing circuitry is further configured to transform the experimental data of the pupillary hippus of the patient via frequency-based transformation, and remove, from the transformed experimental data, data according to a predetermined frequency range.

(19) The apparatus according to any of (11) to (18), wherein the evaluation of the pupillary hippus of the patient can be an identification of a presence of a dysautonomia, the dysautonomia being one selected from a group including postural orthostatic tachycardia syndrome and diabetic neuropathy.

(20) An apparatus for evaluation of a pupillary hippus of a patient, comprising processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on a display and based upon the determination, the evaluation of the pupillary hippus of the patient.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. An apparatus for evaluation of a pupillary hippus of a patient, comprising:
   a display; and
   processing circuitry configured to
      transform experimental data of the pupillary hippus of the patient and reference data via frequency-based transformation,
      calculate a first parameter of one or more selected parameters based upon the transformed experimental data of the pupillary hippus of the patient,
      calculate, based upon the transformed reference data, a corresponding first parameter of the one or more selected parameters,
      generate a metric from the first parameter based upon the experimental data and the corresponding first parameter based upon the reference data, the generated metric being a normalization of the first parameter and the corresponding first parameter,
      determine whether the generated metric achieves a predetermined threshold, the predetermined threshold being related to a biologically-active target, and
      display, on the display and based upon the determination, the evaluation of the pupillary hippus of the patient, wherein
   the evaluation of the pupillary hippus of the patient is an identification of the biologically-active target, the biologically-active target being selected from a group including alcohol, opioids, cannabinols, alpha-2 agonists, benzodiazepines, ketaminemorphine, morphine-3-glucuronide, morphine-6-glucuronide, or a combination thereof.

2. The apparatus according to claim 1, wherein the processing circuitry is further configured to
   determine whether the generated metric achieves the predetermined threshold based upon a correlation between the first parameter of the experimental data and the corresponding first parameter of the reference data.

3. The apparatus according to claim 1, wherein the first parameter based upon the experimental data is an amplitude at a predetermined frequency.

4. The apparatus according to claim 1, wherein the first parameter based upon the experimental data is band power.

5. The apparatus according to claim 1, wherein the generated metric is a difference between a band power of the experimental data and a band power of the reference data.

6. The apparatus according to claim 1, wherein the first parameter based upon the experimental data is a mathematical model of the experimental data.

7. The apparatus according to claim 6, wherein the first parameter based upon the experimental data is a mathematical model of a frequency spectrum of the experimental data.

8. The apparatus according to claim 1, wherein the generated metric is a similarity ratio of mathematical models of a frequency spectrum of the experimental data and of the reference data.

9. The apparatus according to claim 1, wherein the processing circuitry is further configured to
   acquire a plurality of video sequences of an eye of the patient,
   generate pupillary data based upon primary data calculated from the plurality of video sequences, the primary data including time-based pupillary dimensions, and
   calculate, from the generated pupillary data, secondary data, wherein
   the secondary data include the frequency spectrum of the pupillary hippus.

10. The apparatus according to claim 9, wherein the primary data are calculated based upon a mask image, the processing circuitry, in order to generate the mask image, being further configured to
    locate a center of a pupil of the eye, a boundary of the pupil of the eye, and an iris of the eye, and
    generate the mask image, the mask image corresponding to an expected location of the iris based upon the location of the center of the pupil of the eye, the boundary of the pupil of the eye, and the iris of the eye.

11. An apparatus for evaluation of a pupillary hippus of a patient, comprising:
    a display; and
    processing circuitry configured to
       calculate a first parameter of one or more selected parameters based upon experimental data of the pupillary hippus of the patient,
       calculate, based upon reference data of a pupillary hippus, a corresponding first parameter of the one or more selected parameters,
       generate a metric from the first parameter based upon the experimental data and the corresponding first parameter based upon the reference data, the generated metric being a normalization of the first parameter and the corresponding first parameter,
       determine whether the generated metric achieves a predetermined threshold, the predetermined threshold being related to a biologically-active target, and
       display, on the display and based upon the determination, the evaluation of the pupillary hippus of the patient,
    wherein the evaluation of the pupillary hippus of the patient is an identification of the biologically-active target, the biologically-active target being selected from a group including alcohol, opioids, cannabinols, alpha-2 agonists, benzodiazepines, ketaminemorphine, morphine-3-glucuronide, morphine-6-glucuronide, or a combination thereof.

12. The apparatus according to claim 11, wherein the processing circuitry is further configured to
    determine whether the generated metric achieves the predetermined threshold based upon a correlation between the first parameter of the experimental data and the corresponding first parameter of the reference data.

13. The apparatus according to claim 11, wherein the processing circuitry is further configured to
    transform the experimental data of the pupillary hippus of the patient and the reference data via frequency-based transformation, and
    the generated metric is a difference between a band power of the experimental data and a band power of the reference data.

14. The apparatus according to claim 11, wherein the processing circuitry is further configured to transform the experimental data of the pupillary hippus of the patient and the reference data via frequency-based transformation, and the generated metric is a similarity ratio of mathematical models of a frequency spectrum of the experimental data and of the reference data.

15. The apparatus according to claim 11, wherein the processing circuitry is further configured to acquire a plurality of video sequences of an eye of the patient, generate pupillary data based upon primary data calculated from the plurality of video sequences, the primary data including time-based pupillary dimensions, and calculate, from the generated pupillary data, secondary data, wherein the secondary data include the frequency spectrum of the pupillary hippus.

16. The apparatus according to claim 15, wherein the primary data are calculated based upon a mask image, the processing circuitry, in order to generate the mask image, being further configured to locate a center of a pupil of the eye, a boundary of the pupil of the eye, and an iris of the eye, and generate the mask image, the mask image corresponding to an expected location of the iris based upon the location of the center of the pupil of the eye, the boundary of the pupil of the eye, and the iris of the eye.

17. The apparatus according to claim 11, wherein the processing circuitry is further configured to transform the experimental data of the pupillary hippus of the patient via frequency-based transformation, and remove, from the transformed experimental data, data according to a predetermined frequency range.

18. The apparatus according to claim 11, wherein the evaluation of the pupillary hippus of the patient can be an identification of a presence of a dysautonomia, the dysautonomia being one selected from a group including postural orthostatic tachycardia syndrome and diabetic neuropathy.

19. An apparatus for evaluation of a pupillary hippus of a patient, comprising:

processing circuitry configured to calculate a first parameter of one or more selected parameters based upon experimental data of the pupillary hippus of the patient, calculate, based upon reference data of a pupillary hippus, a corresponding first parameter of the one or more selected parameters, generate a metric from the first parameter based upon the experimental data and the corresponding first parameter based upon the reference data, the generated metric being a normalization of the first parameter and the corresponding first parameter, determine whether the generated metric achieves a predetermined threshold, the predetermined threshold being related to a biologically-active target, and display, on a display and based upon the determination, the evaluation of the pupillary hippus of the patient, wherein the evaluation of the pupillary hippus of the patient is an identification of the biologically-active target, the biologically-active target being selected from a group including alcohol, opioids, cannabinols, alpha-2 agonists, benzodiazepines, ketaminemorphine, morphine-3-glucuronide, morphine-6-glucuronide, or a combination thereof.

* * * * *